(12) United States Patent
Rimbaugh et al.

(10) Patent No.: US 7,896,887 B2
(45) Date of Patent: Mar. 1, 2011

(54) APPARATUS AND METHOD FOR DEPLOYMENT OF A BRONCHIAL OBSTRUCTION DEVICE

(75) Inventors: Jenni Rimbaugh, Bothell, WA (US); Lauri J. DeVore, Seattle, WA (US)

(73) Assignee: Spiration, Inc., Redmond, WA (US)

( * ) Notice: Subject to any disclaimer, the term of this patent is extended or adjusted under 35 U.S.C. 154(b) by 693 days.

(21) Appl. No.: 11/733,710

(22) Filed: Apr. 10, 2007

(65) Prior Publication Data

US 2007/0185531 A1  Aug. 9, 2007

Related U.S. Application Data

(63) Continuation of application No. 10/418,929, filed on Apr. 17, 2003, now abandoned, which is a continuation of application No. 10/052,875, filed on Oct. 25, 2001, now Pat. No. 6,592,594.

(51) Int. Cl.
*A61B 17/12* (2006.01)
(52) U.S. Cl. ...................................... 606/108
(58) Field of Classification Search ................. 606/113, 606/114, 127, 159, 191–198; 623/1.11, 1.12, 623/1.2, 1.24
See application file for complete search history.

(56) References Cited

U.S. PATENT DOCUMENTS

| 2,981,254 A | 4/1961 | Vanderbilt |
| 3,540,431 A | 11/1970 | Modin-Uddin |
| 3,657,744 A | 4/1972 | Ersek |
| 3,760,808 A | 9/1973 | Bleuer |
| 3,788,327 A | 1/1974 | Donowitz et al. |
| 3,874,388 A | 4/1975 | King et al. |

(Continued)

FOREIGN PATENT DOCUMENTS

EP  1 151 729 A1  11/2001

(Continued)

OTHER PUBLICATIONS

Article: Autocath ®100—Nonsurgical, Intraurethral Bladder Control Device for Incontinent and Retentive Women—Dr. Kulisz's Development.

(Continued)

*Primary Examiner*—Kevin T Truong
(74) *Attorney, Agent, or Firm*—Knobbe Martens Olson & Bear LLP

(57) ABSTRACT

An apparatus and method deploy a self-expandable bronchial obstruction device in an air passageway. The apparatus includes a catheter configured to be passed down the trachea. The apparatus further includes a capsule for housing the self-expandable bronchial obstruction device in a sterile environment. The capsule is configured to be advanced down the catheter. The capsule further includes a tubular extension. The capsule has a breakable seam so as to release the bronchial obstruction device in the air passageway upon a proximal force being exerted upon the bronchial obstruction device. The method includes guiding a conduit down a trachea into the air passageway. The method further includes advancing a capsule having a bronchial device therein down an internal lumen of the conduit into the air passageway. The method further includes releasing the bronchial device from the capsule. The method further includes deploying the bronchial device into the air passageway.

20 Claims, 3 Drawing Sheets

U.S. PATENT DOCUMENTS

| | | | |
|---|---|---|---|
| 4,014,318 A | 3/1977 | Dockum et al. |
| 4,086,665 A | 5/1978 | Poirier |
| 4,212,463 A | 7/1980 | Repinski et al. |
| 4,250,873 A | 2/1981 | Bonnet |
| 4,302,854 A | 12/1981 | Runge |
| 4,619,246 A | 10/1986 | Molgaard-Nielsen et al. |
| 4,681,110 A | 7/1987 | Wiktor |
| 4,710,192 A | 12/1987 | Liotta et al. |
| 4,732,152 A | 3/1988 | Wallsten et al. |
| 4,759,758 A | 7/1988 | Gabbay |
| 4,795,449 A | 1/1989 | Schneider et al. |
| 4,808,183 A | 2/1989 | Panje |
| 4,819,664 A | 4/1989 | Nazari |
| 4,830,003 A | 5/1989 | Wolff et al. |
| 4,832,680 A | 5/1989 | Haber et al. |
| 4,846,836 A | 7/1989 | Reich |
| 4,850,999 A | 7/1989 | Planck |
| 4,852,568 A | 8/1989 | Kensey |
| 4,877,025 A | 10/1989 | Hanson |
| 4,934,999 A | 6/1990 | Bader |
| 4,968,294 A | 11/1990 | Salama |
| 5,061,274 A | 10/1991 | Kensey |
| 5,116,360 A | 5/1992 | Pinchuk et al. |
| 5,116,564 A | 5/1992 | Jansen et al. |
| 5,123,919 A | 6/1992 | Sauter et al. |
| 5,151,105 A | 9/1992 | Kwan-Gett |
| 5,158,548 A | 10/1992 | Lau et al. |
| 5,161,524 A | 11/1992 | Evans |
| 5,306,234 A | 4/1994 | Johnson |
| 5,352,240 A | 10/1994 | Ross |
| 5,358,518 A | 10/1994 | Camilli |
| 5,366,478 A | 11/1994 | Brinkerhoff et al. |
| 5,382,261 A | 1/1995 | Palmaz |
| 5,392,775 A | 2/1995 | Adkins, Jr. et al. |
| 5,409,019 A | 4/1995 | Wilk |
| 5,411,507 A | 5/1995 | Heckele |
| 5,411,552 A | 5/1995 | Andersen et al. |
| 5,413,599 A | 5/1995 | Imachi et al. |
| 5,417,226 A | 5/1995 | Juma |
| 5,445,626 A | 8/1995 | Gigante |
| 5,453,090 A | 9/1995 | Martinez et al. |
| 5,484,444 A | 1/1996 | Braunschweiler et al. |
| 5,486,154 A | 1/1996 | Kelleher |
| 5,499,995 A | 3/1996 | Teirstein |
| 5,500,014 A | 3/1996 | Quijano et al. |
| 5,549,626 A | 8/1996 | Miller et al. |
| 5,549,628 A | 8/1996 | Cooper et al. |
| 5,562,608 A | 10/1996 | Sekins et al. |
| 5,603,698 A | 2/1997 | Roberts et al. |
| 5,645,565 A | 7/1997 | Rudd et al. |
| 5,647,857 A | 7/1997 | Anderson et al. |
| 5,660,175 A | 8/1997 | Dayal |
| 5,662,713 A | 9/1997 | Andersen et al. |
| 5,683,451 A | 11/1997 | Lenker et al. |
| 5,690,644 A | 11/1997 | Yurek et al. |
| 5,693,089 A | 12/1997 | Inoue |
| 5,697,968 A | 12/1997 | Rogers et al. |
| 5,702,409 A | 12/1997 | Rayburn et al. |
| 5,725,519 A | 3/1998 | Penner et al. |
| 5,752,965 A | 5/1998 | Francis et al. |
| 5,755,770 A | 5/1998 | Ravenscroft |
| 5,797,960 A | 8/1998 | Stevens et al. |
| 5,800,339 A | 9/1998 | Salama |
| 5,810,837 A | 9/1998 | Hofmann et al. |
| 5,817,101 A | 10/1998 | Fiedler |
| 5,830,217 A | 11/1998 | Ryan |
| 5,840,081 A | 11/1998 | Andersen et al. |
| 5,851,232 A | 12/1998 | Lois |
| 5,855,587 A | 1/1999 | Hyon et al. |
| 5,855,597 A | 1/1999 | Jayaraman |
| 5,855,601 A | 1/1999 | Bessler et al. |
| 5,944,738 A | 8/1999 | Amplatz et al. |
| 5,947,997 A | 9/1999 | Pavcnik et al. |
| 5,954,766 A | 9/1999 | Zadno-Azizi et al. |
| 5,957,949 A | 9/1999 | Leonhardt et al. |
| 5,972,009 A | 10/1999 | Fortier et al. |
| 5,976,158 A | 11/1999 | Adams et al. |
| 5,976,174 A | 11/1999 | Ruiz |
| 5,984,965 A | 11/1999 | Knapp et al. |
| 6,003,517 A | 12/1999 | Sheffield et al. |
| 6,007,575 A | 12/1999 | Samuels |
| 6,009,614 A | 1/2000 | Morales |
| 6,020,380 A | 2/2000 | Killian |
| 6,027,525 A | 2/2000 | Suh et al. |
| 6,045,560 A | 4/2000 | McKean et al. |
| 6,051,022 A | 4/2000 | Cai et al. |
| 6,068,635 A | 5/2000 | Gianotti |
| 6,068,638 A | 5/2000 | Makower |
| 6,077,291 A | 6/2000 | Das |
| 6,083,255 A | 7/2000 | Laufer et al. |
| 6,096,027 A * | 8/2000 | Layne ........................ 606/1 |
| 6,099,551 A | 8/2000 | Gabbay |
| 6,123,663 A | 9/2000 | Rebuffat |
| 6,135,729 A | 10/2000 | Aber |
| 6,135,991 A | 10/2000 | Muni et al. |
| 6,141,855 A | 11/2000 | Morales |
| 6,149,664 A | 11/2000 | Kurz |
| 6,162,245 A | 12/2000 | Jayaraman |
| 6,165,179 A | 12/2000 | Cathcart et al. |
| 6,168,614 B1 | 1/2001 | Andersen et al. |
| 6,168,617 B1 | 1/2001 | Blaeser et al. |
| 6,174,323 B1 | 1/2001 | Biggs |
| 6,183,520 B1 | 2/2001 | Pintauro et al. |
| 6,200,333 B1 | 3/2001 | Laufer |
| 6,206,918 B1 | 3/2001 | Campbell et al. |
| 6,234,996 B1 | 5/2001 | Bagaoisan et al. |
| 6,240,615 B1 | 6/2001 | Kimes et al. |
| 6,241,758 B1 | 6/2001 | Cox |
| 6,245,102 B1 | 6/2001 | Jayaraman |
| 6,258,100 B1 | 7/2001 | Alferness et al. |
| 6,270,527 B1 | 8/2001 | Campbell et al. |
| 6,287,290 B1 | 9/2001 | Perkins et al. |
| 6,287,334 B1 | 9/2001 | Moll et al. |
| 6,293,951 B1 | 9/2001 | Alferness et al. |
| 6,302,893 B1 | 10/2001 | Limon et al. |
| 6,312,407 B1 | 11/2001 | Zadno-Azizi et al. |
| 6,325,777 B1 | 12/2001 | Zadno-Azizi et al. |
| 6,325,778 B1 | 12/2001 | Zadno-Azizi et al. |
| 6,327,772 B1 | 12/2001 | Zadno-Azizi et al. |
| 6,328,689 B1 | 12/2001 | Gonzalez et al. |
| 6,350,278 B1 * | 2/2002 | Lenker et al. .............. 623/1.12 |
| 6,355,014 B1 | 3/2002 | Zadno-Azizi et al. |
| 6,398,775 B1 | 6/2002 | Perkins et al. |
| 6,402,754 B1 | 6/2002 | Gonzalez |
| 6,416,554 B1 | 7/2002 | Alferness et al. |
| 6,428,561 B1 | 8/2002 | Johansson-Ruden et al. |
| 6,439,233 B1 | 8/2002 | Geertsema |
| 6,458,076 B1 | 10/2002 | Pruitt |
| 6,485,407 B2 | 11/2002 | Alferness et al. |
| 6,488,673 B1 | 12/2002 | Laufer |
| 6,491,706 B1 | 12/2002 | Alferness et al. |
| 6,493,589 B1 | 12/2002 | Medhkour et al. |
| 6,510,846 B1 | 1/2003 | O'Rourke |
| 6,514,290 B1 | 2/2003 | Loomas |
| 6,527,761 B1 | 3/2003 | Soltesz et al. |
| 6,540,782 B1 | 4/2003 | Snyders |
| 6,585,639 B1 | 7/2003 | Kotmel et al. |
| 6,592,594 B2 | 7/2003 | Rimbaugh et al. |
| 6,599,311 B1 | 7/2003 | Biggs et al. |
| 6,610,043 B1 | 8/2003 | Ingenito |
| 6,629,951 B2 | 10/2003 | Laufer et al. |
| 6,634,363 B1 | 10/2003 | Laufer et al. |
| 6,638,285 B2 | 10/2003 | Gabbay |
| 6,679,264 B1 | 1/2004 | Deem et al. |

| | | | |
|---|---|---|---|
| 6,694,979 B2 | 2/2004 | Deem et al. | |
| 2001/0025132 A1 | 9/2001 | Alferness et al. | |
| 2001/0037808 A1 | 11/2001 | Deem et al. | |
| 2001/0041906 A1 | 11/2001 | Gonzalez | |
| 2001/0051799 A1 | 12/2001 | Ingenito | |
| 2001/0052344 A1 | 12/2001 | Doshi | |
| 2001/0056274 A1 | 12/2001 | Perkins et al. | |
| 2002/0007831 A1 | 1/2002 | Davenport et al. | |
| 2002/0062120 A1 | 5/2002 | Perkins et al. | |
| 2002/0077593 A1 | 6/2002 | Perkins et al. | |
| 2002/0077696 A1 | 6/2002 | Zadno-Azizi et al. | |
| 2002/0087153 A1 | 7/2002 | Roschak et al. | |
| 2002/0095209 A1 | 7/2002 | Zadno-Azizi et al. | |
| 2002/0111619 A1 | 8/2002 | Keast et al. | |
| 2002/0111620 A1 | 8/2002 | Cooper et al. | |
| 2002/0112729 A1 | 8/2002 | DeVore et al. | |
| 2002/0138135 A1 | 9/2002 | Duerig et al. | |
| 2002/0147462 A1 | 10/2002 | Mair et al. | |
| 2003/0018327 A1 | 1/2003 | Truckai et al. | |
| 2003/0018344 A1 | 1/2003 | Kaji et al. | |
| 2003/0024527 A1 | 2/2003 | Ginn | |
| 2003/0050648 A1 | 3/2003 | Alferness et al. | |
| 2003/0051733 A1 | 3/2003 | Kotmel et al. | |
| 2003/0055331 A1 | 3/2003 | Kotmel et al. | |
| 2003/0070682 A1 | 4/2003 | Wilson et al. | |
| 2003/0083671 A1 | 5/2003 | Rimbaugh et al. | |
| 2003/0127090 A1 | 7/2003 | Gifford et al. | |
| 2003/0154988 A1 | 8/2003 | DeVore et al. | |
| 2003/0158515 A1 | 8/2003 | Gonzalez et al. | |
| 2003/0228344 A1 | 12/2003 | Fields et al. | |
| 2004/0039250 A1 | 2/2004 | Tholfsen et al. | |
| 2005/0137611 A1 | 6/2005 | Escudero et al. | |
| 2005/0267323 A1 | 12/2005 | Dorros et al. | |

FOREIGN PATENT DOCUMENTS

| | | | |
|---|---|---|---|
| EP | 1157663 A1 | | 11/2001 |
| GB | 2 324 729 A | | 11/1998 |
| GB | 2324729 A | * | 11/1998 |
| RU | 2140211 | | 10/1999 |
| SU | 852321 | | 8/1981 |
| WO | WO 94/26175 A1 | | 11/1994 |
| WO | WO 95/32018 A1 | | 11/1995 |
| WO | WO 96/34582 A1 | | 11/1996 |
| WO | WO 97/44085 A2 | | 11/1997 |
| WO | WO 98/00840 A1 | | 1/1998 |
| WO | WO 98/19633 A1 | | 5/1998 |
| WO | WO 98/39047 A1 | | 9/1998 |
| WO | WO 98/44854 A1 | | 10/1998 |
| WO | WO 98/48706 A1 | | 11/1998 |
| WO | WO 99/01076 A1 | | 1/1999 |
| WO | WO 99/13801 A1 | | 3/1999 |
| WO | WO 99/26692 A1 | | 6/1999 |
| WO | WO 99/32040 A1 | | 7/1999 |
| WO | WO 99/42059 A2 | | 8/1999 |
| WO | WO 99/42161 A2 | | 8/1999 |
| WO | WO 99/64109 A1 | | 12/1999 |
| WO | WO 00/42950 A2 | | 7/2000 |
| WO | WO 00/51510 | | 9/2000 |
| WO | WO 00/51510 A1 | | 9/2000 |
| WO | WO 00/62699 A2 | | 10/2000 |
| WO | WO 00/78386 A1 | | 12/2000 |
| WO | WO 00/78407 A1 | | 12/2000 |
| WO | WO 01/02042 A1 | | 1/2001 |
| WO | WO 01/03642 A1 | | 1/2001 |
| WO | WO 01/05334 A1 | | 1/2001 |
| WO | WO 01/10313 A1 | | 2/2001 |
| WO | WO 01/10314 A1 | | 2/2001 |
| WO | WO 01/12104 A1 | | 2/2001 |
| WO | WO 01/13839 A1 | | 3/2001 |
| WO | WO 01/13908 | | 3/2001 |
| WO | WO 01/28433 A1 | | 4/2001 |
| WO | WO 01/45590 A2 | | 6/2001 |
| WO | WO 01/49213 A2 | | 7/2001 |
| WO | WO 01/52775 A1 | | 7/2001 |
| WO | WO 01/54585 A1 | | 8/2001 |
| WO | WO 01/54625 A1 | | 8/2001 |
| WO | WO 01/54685 A1 | | 8/2001 |
| WO | WO 01/66190 | | 9/2001 |
| WO | WO 01/74271 A1 | | 10/2001 |
| WO | WO 01/87170 A1 | | 11/2001 |
| WO | WO 01/89366 A2 | | 11/2001 |
| WO | WO 01/95786 A2 | | 12/2001 |
| WO | WO 02/05884 A2 | | 1/2002 |
| WO | WO 02/22072 | | 3/2002 |
| WO | WO 02/32333 A1 | | 4/2002 |
| WO | WO 02/34322 A2 | | 5/2002 |
| WO | WO 02/38038 | | 5/2002 |
| WO | WO 02/47575 A2 | | 6/2002 |
| WO | WO 02/056794 A2 | | 7/2002 |
| WO | WO 02/064045 A1 | | 8/2002 |
| WO | WO 02/064190 A3 | | 8/2002 |
| WO | WO 02/069823 | | 9/2002 |
| WO | WO 02/094087 A1 | | 11/2002 |
| WO | WO 03/022124 | | 3/2003 |
| WO | WO 03/030975 | | 4/2003 |
| WO | WO 03/034927 | | 5/2003 |
| WO | WO 03/041779 A1 | | 5/2003 |
| WO | WO 03/047468 A1 | | 6/2003 |
| WO | WO 03/078579 A2 | | 9/2003 |
| WO | WO 03/088820 A2 | | 10/2003 |
| WO | WO 03/099164 | | 12/2003 |
| WO | WO 03/099164 A1 | | 12/2003 |
| WO | WO 2004/010845 A2 | | 2/2004 |
| WO | WO 2004/010845 | | 5/2004 |

OTHER PUBLICATIONS

Dillard et al., "Evaluation of a Novel Intra-bronchial Valve Device to Produce Lung Volume Reduction," Poster shown at conference in Jun. 2002.

EWS Endobronchial Watanabe Spigots, Novatech, edited Apr. 17, 2002.

Harris et al., "The Experimental Production in Dogs of Emphysema with Associated Asthmatic Syndrome by Means of an Intratracheal Ball Valve," J. Exp Med 30:1919; 75-88.

Horiuchi et al: Three Cases of Intractable Pneumothorax Treated Successfully by Bronchial Embolization using Silicon; JJSB, 2001. pp. 25-30.

Inaspettato: Endoscopic Treatment of Bronchopleural Fistulas Using N-butyl-2-cyanoacrylate; Surgical Laparoscopy & Endoscopy; vol. 4 No. 1, pp. 62-64, 1994.

Jones et al: Closure of a Benign Broncho-Oesophageal Fistula by Endoscopic Injection of Bovine Collagen, Cyanocrylate Glue and Gelfoam; 1996, pp. 53-55 Aust. N. Z. J. Surg.

Lewis et al., "Pulmonary Interstitial Emphysema: Selective Bronchial Occlusion with a Swan-Ganz Catheter." Archives of Disease in Childhood, 63:1988, 313-315.

Mathew et al. "Selective Bronchial Obstruction for Treatment of Bullous Interstitial Emphysema," J. of Ped. 96:1980, 475-477.

Okada et al: Emergent Bronchofiberoptic Bronchial Occlusion for Intractable Pneumothorax with Severe Emphysema; The Japanese Journal of Thoracic and Cardiovascular Surgery, 1998. pp. 1078-1081.

Puhakka et al., "Acute Bronchial Obstruction: An Experimental Rabbit Model Study." Int. J. Of Pediatric Otorhinolaryngology. 18:1989, 107-118.

Snider et al., "The Definition of Emphysema: Report of the National Heart Lung and Blood Institute, Division of Lung Diseases Workshop", Am. Rev. Respir. Dis., 132:182-185, 1985.

Watanabe et al: Bronchial Embolization Using Dental Impression Material in a Case of Pyelo-bronchial Fistula with Candida Fungemia; 1991. Journal of the Japan Society for Bronchology, pp. 607-610.

* cited by examiner

FIG. 1
FIG. 2
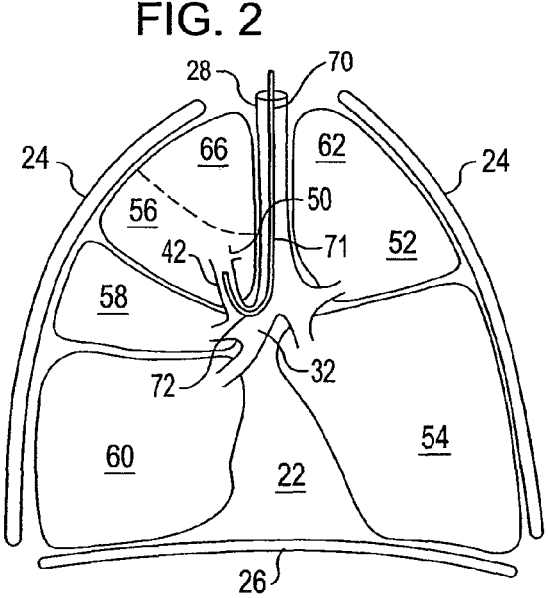
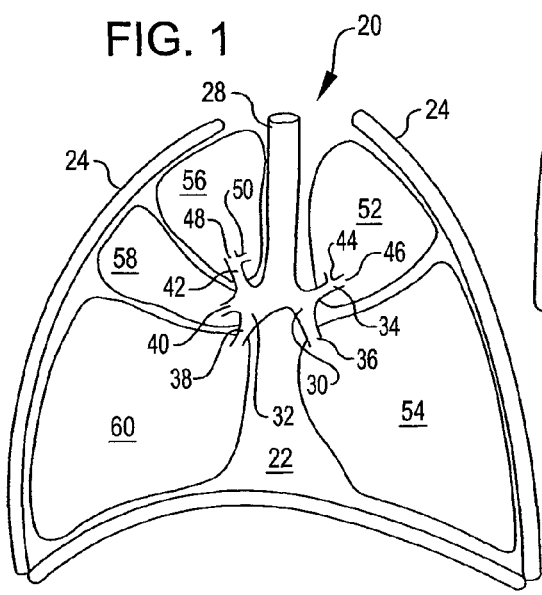
FIG. 3
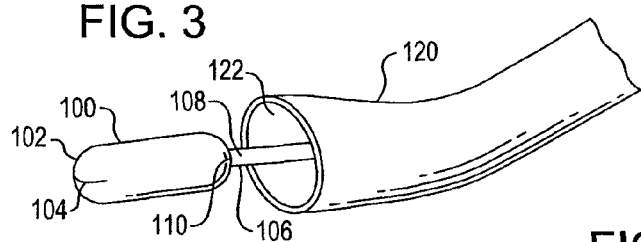
FIG. 4
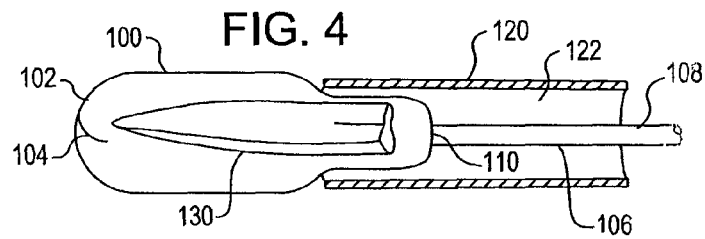
FIG. 5
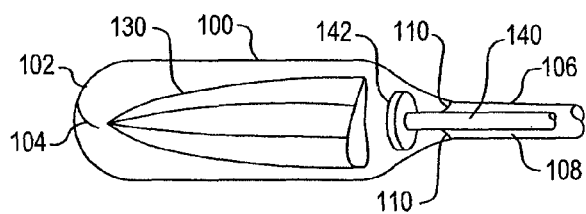

APPARATUS AND METHOD FOR DEPLOYMENT OF A BRONCHIAL OBSTRUCTION DEVICE

CROSS-REFERENCE TO RELATED APPLICATIONS

This application is a continuation of U.S. patent application Ser. No. 10/418,929, filed Apr. 17, 2003, now abandoned titled BRONCHIAL OBSTRUCTION DEVICE DEPLOYMENT SYSTEM AND METHOD, which is a continuation of U.S. patent application Ser. No. 10/052,875, filed on Oct. 25, 2001, now U.S. Pat. No. 6,592,594, titled BRONCHIAL OBSTRUCTION DEVICE DEPLOYMENT SYSTEM AND METHOD. The entire disclosure of each of the above-noted prior applications is hereby incorporated by reference herein and made a part of this specification.

BACKGROUND OF THE INVENTION

1. Field of the Invention

The present invention is generally directed to a treatment of Chronic Obstructive Pulmonary Disease (COPD). The present invention is more particularly directed to an apparatus and method for deploying a bronchial device.

2. Description of the Related Art

Chronic Obstructive Pulmonary Disease (COPD) has become a major cause of morbidity and mortality in the United States over the last three decades. COPD is characterized by the presence of airflow obstruction due to chronic bronchitis or emphysema. The airflow obstruction in COPD is due largely to structural abnormalities in the smaller airways. Important causes are inflammation, fibrosis, goblet cell metaplasia, and smooth muscle hypertrophy in terminal bronchioles.

The incidence, prevalence, and health-related costs of COPD are on the rise. Mortality due to COPD is also on the rise. In 1991 COPD was the fourth leading cause of death in the United States and has increased 33% since 1979.

COPD affects the patient's whole life. It has three main symptoms: cough; breathlessness; and wheeze. At first, breathlessness may be noticed when running for a bus, digging in the garden, or walking up a hill. Later, it may be noticed when simply walking in the kitchen. Over time, it may occur with less and less effort until it is present all of the time.

COPD is a progressive disease and currently has no cure. Current treatments for COPD include the prevention of further respiratory damage, pharmacotherapy, and surgery. Each is discussed below.

The prevention of further respiratory damage entails the adoption of a healthy lifestyle. Smoking cessation is believed to be the single most important therapeutic intervention. However, regular exercise and weight control are also important. Patients whose symptoms restrict their daily activities or who otherwise have an impaired quality of life may require a pulmonary rehabilitation program including ventilatory muscle training and breathing retraining. Long-term oxygen therapy may also become necessary.

Pharmacotherapy may include bronchodilator therapy to open up the airways as much as possible or inhaled β-agonists. For those patients who respond poorly to the foregoing or who have persistent symptoms, Ipratropium bromide may be indicated. Further, courses of steroids, such as corticosteroids, may be required. Lastly, antibiotics may be required to prevent infections, and influenza and pneumococcal vaccines may be routinely administered. Unfortunately, there is no evidence that early, regular use of pharmacotherapy will alter the progression of COPD.

About 40 years ago, it was first postulated that the tethering force that tends to keep the intrathoracic airways open was lost in emphysema and that by surgically removing the most affected parts of the lungs, the force could be partially restored. Although the surgery was deemed promising, the procedure was abandoned.

The lung volume reduction surgery (LVRS) was later revived. In the early 1990's, hundreds of patients underwent the procedure. However, the procedure has fallen out of favor due to the fact that Medicare stopping reimbursing for LVRS. Unfortunately, data is relatively scarce and many factors conspire to make what data exists difficult to interpret. The procedure is currently under review in a controlled clinical trial. What data does exist tends to indicate that patients benefited from the procedure in terms of an increase in forced expiratory volume, a decrease in total lung capacity, and a significant improvement in lung function, dyspnea, and quality of life. However, the surgery is not without potential complications. Lung tissue is very thin and fragile. Hence, it is difficult to suture after sectioning. This gives rise to potential infection and air leaks. In fact, nearly thirty percent (30%) of such surgeries result in air leaks.

Improvements in pulmonary functions after LVRS have been attributed to at least four possible mechanisms. These include enhanced elastic recoil, correction of ventilation/perfusion mismatch, improved efficiency of respiratory musculature, and improved right ventricular filling.

Lastly, lung transplantation is also an option. Today, COPD is the most common diagnosis for which lung transplantation is considered. Unfortunately, this consideration is given for only those with advanced COPD. Given the limited availability of donor organs, lung transplant is far from being available to all parties.

In view of the need in the art for new and improved therapies for COPD which provide more permanent results than pharmacotherapy while being less invasive and traumatic than LVRS, at least two new therapies have recently been proposed. Both of these new therapies provide lung size reduction by permanently or temporarily collapsing at least a portion of a lung.

In accordance with a first one of these therapies, and as described in U.S. Pat. No. 6,258,100 assigned to the assignee of the present invention and incorporated herein by reference, a lung may be collapsed by obstructing an air passageway communicating with the lung portion to be collapsed. The air passageway may be obstructed by placing a bronchial obstruction device in the air passageway. The bronchial obstruction device may be a plug-like device which precludes air flow in both directions or a one-way valve which permits air to be exhaled from the lung portion to be collapsed while precluding air from being inhaled into the lung portion. Once the air passageway is sealed, the residual air within the lung will be absorbed over time to cause the lung portion to collapse.

As further described in U.S. Pat. No. 6,258,100, the lung portion may be collapsed by inserting a conduit into the air passageway communicating with the lung portion to be collapsed. An obstruction device, such as a one-way valve is then advanced down the conduit into the air passageway. The obstruction device is then deployed in the air passageway for sealing the air passageway and causing the lung portion to be collapsed.

The second therapy is fully described in copending U.S. patent application Ser. No. 09/534,244, filed Mar. 23, 2000, for LUNG CONSTRICTION APPARATUS AND METHOD and is also assigned to the assignee of the present invention. As described therein, a lung constriction device including a sleeve of elastic material is configured to cover at least a portion of a lung. The sleeve has a pair of opened ends to permit the lung portion to be drawn into the sleeve. Once drawn therein, the lung portion is constricted by the sleeve to reduce the size of the lung portion.

Both therapies hold great promise for treating COPD. Neither therapy requires sectioning and suturing of lung tissue.

While either therapy alone would be effective in providing lung size reduction and treatment of COPD, it has recently been proposed that the therapies may be combined for more effective treatment. More specifically, it has been proposed that the therapies could be administered in series, with the first mentioned therapy first applied acutely for evaluation of the effectiveness of lung size reduction in a patient and which lung portions should be reduced in size to obtain the best results. The first therapy is ideal for this as it is noninvasive and could be administered in a physician's office. Once the effectiveness of lung size reduction is confirmed and the identity of the lung portions to be collapsed is determined, the more invasive second mentioned therapy may be administered In order to employ the first-mentioned therapy described in U.S. Pat. No. 6,258,100, it is necessary to deploy the bronchial obstruction device within an air passageway. The deployment must be reliable in that the bronchial device must be deployed in a well-controlled manner to assure placement in the proper location. The bronchial device must also be deployed in a sterile manner. Patients suffering from COPD generally have compromised health. Sterile deployment may therefore prevent a catastrophic infection from occurring in those patients who are in a weakened state. The present invention addresses these issues by providing bronchial obstruction device deployment systems and methods which provide more reliable device placement and sterile deployment conditions.

SUMMARY OF THE INVENTION

The present invention provides a device for deploying a self-expandable bronchial obstruction device in an air passageway. The device includes a catheter configured to be passed down the trachea. The device further includes a capsule for housing the self-expandable bronchial obstruction device in a sterile environment. The capsule is further configured to be advanced down the catheter. The capsule further includes a tubular extension. The capsule has a breakable seam so as to release the bronchial device in the air passageway upon a proximal force being exerted upon the bronchial obstruction device. Additionally, the capsule may be formed of flexible material for collapsing within the catheter.

The invention still further provides a method of deploying a bronchial device in an air passageway. The method includes guiding a conduit down a trachea into the air passageway. The method further includes advancing a capsule having a bronchial device therein down an internal lumen of the conduit into the air passageway. The method further includes releasing the bronchial device from the capsule. The method further includes deploying the bronchial device into the air passageway. Additionally, the capsule may comprise a breakable seam from which the bronchial device can be released. The method may further comprise pushing the bronchial device from the capsule.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like referenced numerals identify identical elements, and wherein:

FIG. 1 is a simplified sectional view of a thorax illustrating a healthy respiratory system;

FIG. 2 is a sectional view similar to FIG. 1, but illustrating a respiratory system suffering from COPD and the execution of a first step in treating the COPD condition in accordance with the present invention;

FIG. 3 is a perspective view, illustrating a housing for the bronchial obstruction device and a conduit embodying the present invention;

FIG. 4 is a partial cross-sectional view of the housing exiting the distal end of the conduit;

FIG. 5 is a side view illustrating a pusher just prior to engaging the bronchial obstruction device;

DETAILED DESCRIPTION OF THE PREFERRED EMBODIMENT

Figure 6:
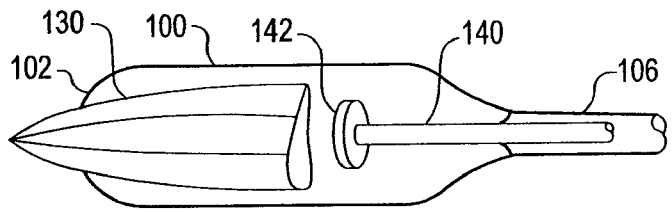
FIG. 6 is another side view illustrating the device being released from the housing by the pusher.

Referring now to FIG. 1, it is a sectional view of a healthy respiratory system. The respiratory system 20 resides within the thorax 22 which occupies a space defined by the chest wall 24 and the diaphragm 26.

The respiratory system 20 includes the trachea 28, the left mainstem bronchus 30, the right mainstem bronchus 32, the bronchial branches 34, 36, 38, 40, and 42 and sub-branches 44, 46, 48, and 50. The respiratory system 20 further includes left lung lobes 52 and 54 and right lung lobes 56, 58, and 60. Each bronchial branch and sub-branch communicates with a respective different portion of a lung lobe, either the entire lung lobe or a portion thereof. As used herein, the term "air passageway" is meant to denote either a bronchial branch or sub-branch which communicates with a corresponding individual lung lobe or lung lobe portion to provide inhaled air thereto or conduct exhaled air therefrom.

Characteristic of a healthy respiratory system is the arched or inwardly arcuate diaphragm 26. As the individual inhales, the diaphragm 26 straightens to increase the volume of the thorax 22. This causes a negative pressure within the thorax. The negative pressure within the thorax in turn causes the lung lobes to fill with air. When the individual exhales, the diaphragm returns to its original arched condition to decrease the volume of the thorax. The decreased volume of the thorax causes a positive pressure within the thorax which in turn causes exhalation of the lung lobes.

In contrast to the healthy respiratory system of FIG. 1, FIG. 2 illustrates a respiratory system suffering from COPD. Here it may be seen that the lung lobes 52, 54, 56, 58, and 60 are enlarged and that the diaphragm 26 is not arched but substantially straight. Hence, this individual is incapable of breathing normally by moving the diaphragm 28. Instead, in order to create the negative pressure in the thorax 22 required for breathing, this individual must move the chest wall outwardly to increase the volume of the thorax. This results in inefficient breathing causing these individuals to breathe rapidly with shallow breaths. It has been found that the apex portion 62 and 66 of the upper lung lobes 52 and 56, respectively, are most affected by COPD.

In accordance with the present invention, COPD treatment or evaluation is initiated by feeding a conduit 70 down the trachea 28, into a mainstream bronchus such as the right mainstem bronchus 32, and into an air passageway such as the bronchial branch 42 or the bronchial sub-branch 50. The conduit 70 may be a catheter or a bronchoscope as are well-known in the art. A bronchial obstruction device, contained within a housing, is then advanced down an internal lumen 71 of the conduit 70 and then released from the housing in the air passageway. Once deployed, the obstruction device precludes inhaled air from entering the lung portion to be collapsed. It is preferable that the obstruction device take the form of a one-way valve. In addition to precluding inhaled air from entering the lung portion, the device further allows air within the lung portion to be exhaled. This results in more rapid collapse of the lung portion. However, obstruction devices which preclude both inhaled and exhaled air flow may be deployed by the apparatus and method of the invention.

FIGS. 3 and 4 show a bronchial obstruction device housing 100 and a conduit 120 embodying the present invention. The housing 100 forms a sealed capsule structure for housing a bronchial obstruction device 130 to be deployed within an air passageway. The housing 100 has a rounded distal end 102. The rounded configuration of the distal end 102 assists in the guiding of the housing to a desired location within the air passageway. The housing 100, as best seen in FIG. 4 is formed of a flexible, biocompatible material for collapsing within the internal lumen 122 of the conduit 120 as it is advanced through the conduit.

The housing distal end 102 further includes a score or notch 104 to enable the distal end 104 of the housing 100 to be broken-away during deployment of the device 130 without breaking the seal within the housing 100 until the time of deployment.

The housing still further includes a tubular extension 106 having an internal lumen 108. The lumen 108 communicates with the interior of the housing 100 during deployment of the device 130 but may be separated therefrom by a breakable wall 110. As will be seen subsequently, the breakable wall 110 maintains the seal of the housing while permitting a pusher to be advanced through the lumen 108 to break through the wall 110 at the time of deployment to then engage the device 130. With the device 130 thus engaged, further distal advancement of the pusher causes the device to break through the distal end 102 of the housing weakened by the notch 104. Still further advancement of the pusher then releases the device 130 from the housing 100 for deployment of the device 130 at the desired location within the air passageway.

Hence, the device 130 may be deployed in a controlled manner. Further, the seal of the housing 100 is not broken until the time of deployment, rendering the process sterile.

Figure 7:
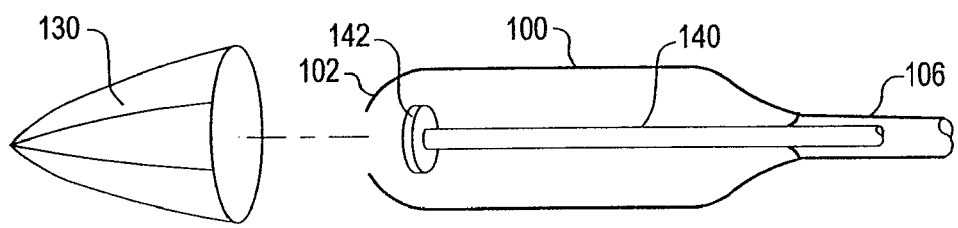
FIG. 7 is another side view of the device, the housing, and the pusher immediately after the device is released from the housing.

FIGS. 5-7 better illustrate the foregoing process. In FIG. 5 it may be seen that the pusher 140 has been advanced through the lumen 108 of the extension 106 and has broken through the wall 110 previously separating the housing 100 from the lumen 108. In accordance with this embodiment, the pusher includes a disc-shaped end 142 for engaging the device 130. Alternatively, the pusher 140 may be an appropriately shaped wire or rod. The end 142 may have a diameter dimension slightly less than the diameter dimension of the lumen 108. Alternatively, the extension 106 may be formed of material flexible enough to permit the end 142 to be slightly greater than the diameter of the lumen 108. This allows the extension 106 to be slightly deformed as the end 142 of the pusher 140 is advanced down the extension. In either arrangement, the pusher is slidable down the extension to break through the wall 110 and enter the housing 100.

As seen in FIG. 6, once the pusher end 142 is within the housing 100, it then engages the device 130 upon further distal advancement. The pusher 140 then pushes the device 130 distally to break through the breakaway distal end 102 of the housing 100.

Further advancement of the pusher 140 causes the device 130 to be released from the housing. Once released, the device 130 is permitted to expand for deployment. Such a device is shown and described in the aforementioned U.S. Pat. No. 6,258,100. As previously mentioned, other forms of bronchial obstruction devices may be deployed with the present invention. Such devices may be one-way valves, totally blocking, expandable, or non-expandable.

Figure 8:
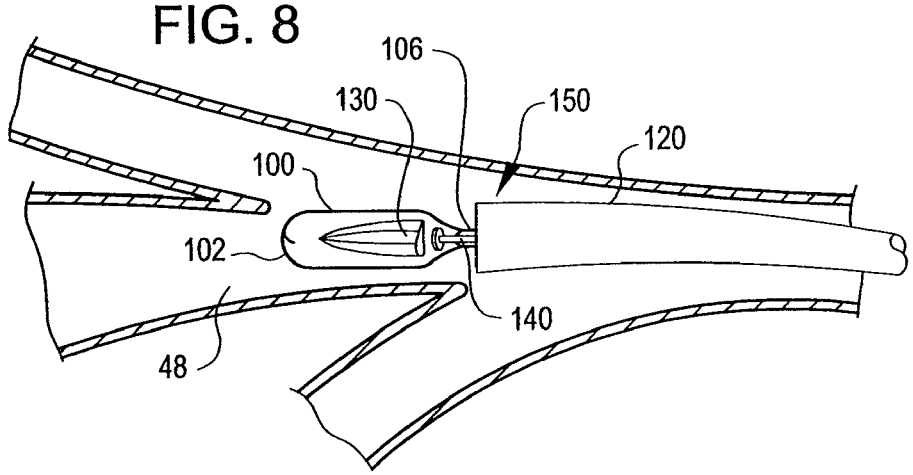
FIG. 8 is a side view illustrating an intermediate step in deploying a bronchial obstruction device in accordance with an embodiment of the present invention.
Figure 9:
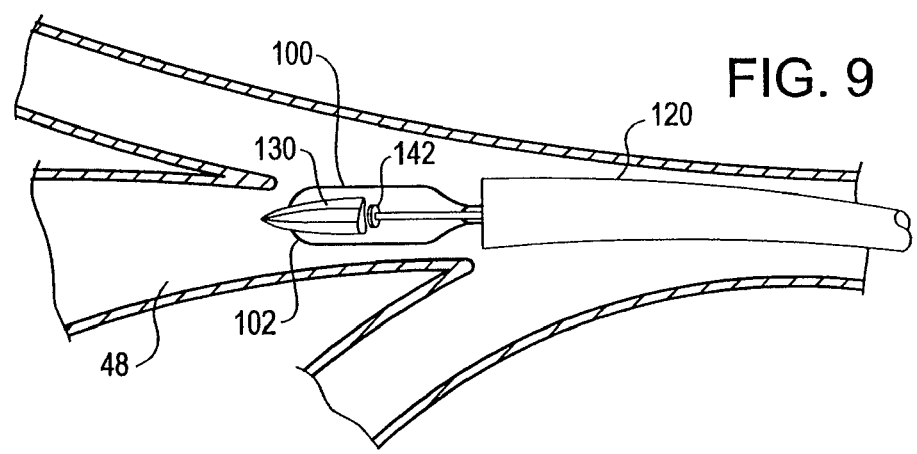
FIG. 9 is another side view illustrating a further step in the deployment of the device.
Figure 10:
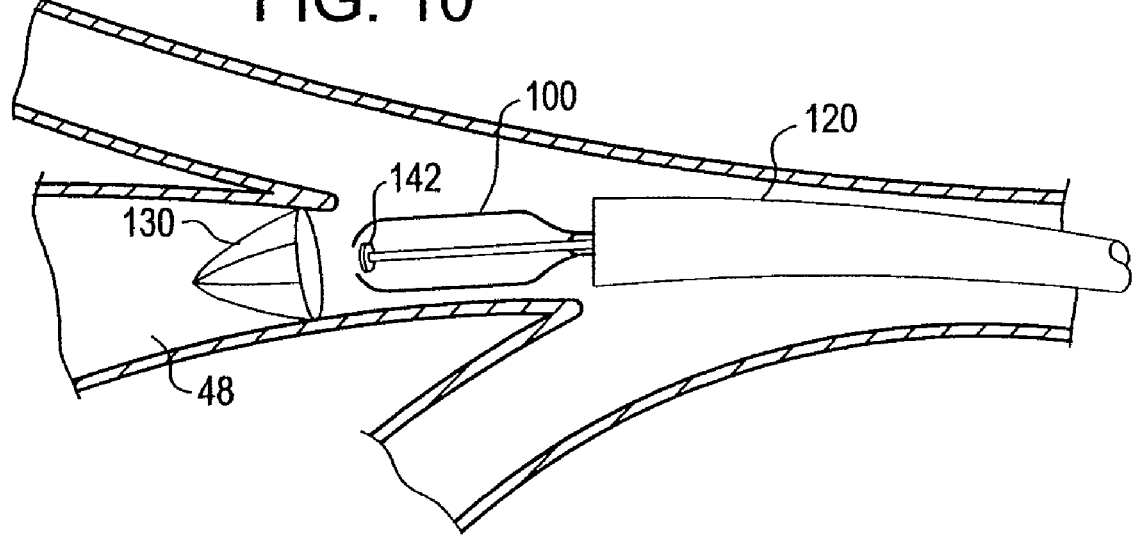
FIG. 10 is a side view illustrating the device after deployment.

FIGS. 8-10 show a complete system 150 embodying the present invention deploying the device 130 within an air passageway, such as bronchial branch sub-branch 48. The system 150 generally includes the conduit 120, the housing 100, the housing extension 106, and the pusher 140 as previously described. In FIG. 8 it may be seen that the conduit 120 has been advanced such that its distal end is just proximal to the bronchial sub-branch 48. The housing 100 has also been advanced through the conduit so that its distal end 102 is within the bronchial sub-branch 48. The pusher has also been advanced into the housing 100 for engagement with the device 130.

As seen in FIG. 9, the pusher end 142 is within the housing 100. It then engages the device 130 and upon further distal advancement, the pusher 140 pushes the device 130 distally to break through the breakaway distal end 102 of the housing 100.

Further advancement of the pusher 140 causes the device 130 to be released from the housing in the bronchial sub-branch 48. Once released, the device 130 is permitted to expand for deployment in the bronchial sub-branch 48. Again, the device 130 may be of the type shown and described in the aforementioned U.S. Pat. No. 6,258,100. The now expanded device 130 serves to obstruct the bronchial sub-branch 48 for collapsing the lung portion communicating with the bronchial sub-branch 48.

Although the invention(s) presented herein have been disclosed in the context of certain preferred embodiments and examples, it will be understood by those skilled in the art that the invention(s) extend beyond the specifically disclosed embodiments to other alternative embodiments and/or uses of the invention(s) and obvious modifications and equivalents thereof. Thus, it is intended that the scope of the invention(s) herein disclosed should not be limited by the particular embodiments described above, but should be determined only by a fair reading of the claims that follow.

What is claimed is:

1. An apparatus for deploying a self-expandable bronchial obstruction device in an air passageway comprising:

a catheter configured to be passed down the trachea;

a sealed capsule for housing the self-expandable bronchial obstruction device in a sterile environment, the capsule being configured to be advanced down the catheter and comprising a tubular extension, the capsule having a breakable seam opened by the self-expandable bronchial obstruction device so as to release the bronchial obstruction device in the air passageway upon a proximal force being exerted upon said self-expandable bronchial obstruction device, wherein the self-expandable bronchial obstruction device is a one-way valve configured to preclude inhaled air from entering an area of the air passageway while allowing air within the area of the air passageway to be exhaled.

2. The apparatus of claim 1 wherein the capsule is formed of flexible material for collapsing within the catheter.

3. The apparatus of claim 1, wherein the sealed capsule comprises a flexible, biocompatible material.

4. The apparatus of claim 1, wherein the sealed capsule comprises a rounded distal end to minimize friction.

5. The apparatus of claim 1, wherein the breakable seam comprises a score or notch.

6. The apparatus of claim 1, wherein the proximal force is applied by a distal end of the sealed capsule.

7. The apparatus of claim 1, further comprises a pusher for engaging the self-expandable bronchial obstruction device.

8. The apparatus of claim 7, wherein the pusher is configured to enable the self-expandable bronchial obstruction device to open the breakable seam.

9. The apparatus of claim 7, wherein the pusher is configured to apply a distal force on the self-expandable bronchial obstruction device to open the breakable seam.

10. The apparatus of claim 7, wherein the pusher comprises a disc-shaped distal end.

11. A method of deploying a bronchial device in an air passageway comprising:

guiding a conduit down a trachea into the air passageway;

advancing a sealed capsule having a sterile environment for storing a self-expandable bronchial obstruction device therein down an internal lumen of the conduit into the air passageway, the sealed capsule having a breakable seam opened by the self-expandable bronchial obstruction device, wherein the self-expandable bronchial obstruction device is a one-way valve configured to preclude inhaled air from entering an area of the air passageway while allowing air within the area of the air passageway to be exhaled;

releasing the self-expandable bronchial obstruction device from the sealed capsule when a proximal force is exerted on the self-expandable bronchial obstruction device; and deploying the self-expandable bronchial obstruction device into the air passageway.

12. The method of claim 11 further comprising pushing the bronchial device from the capsule.

13. The method of claim 11, wherein the sealed capsule comprises a flexible, biocompatible material.

14. The method of claim 11, wherein the sealed capsule comprises a rounded distal end to minimize friction.

15. The method of claim 11, wherein the breakable seam comprises a score or notch.

16. The method of claim 11, wherein the proximal force is applied by a distal end of the sealed capsule.

17. The method of claim 11, wherein the releasing further comprises engaging the self-expandable bronchial obstruction device with a pusher.

18. The apparatus of claim 17, wherein the pusher is configured to enable the self-expandable bronchial obstruction device to open the breakable seam.

19. The apparatus of claim 17, wherein the pusher is configured to apply a distal force on the self-expandable bronchial obstruction device to open the breakable seam.

20. The apparatus of claim 17, wherein the pusher comprises a disc-shaped distal end.

* * * * *

UNITED STATES PATENT AND TRADEMARK OFFICE
CERTIFICATE OF CORRECTION

PATENT NO.         : 7,896,887 B2
APPLICATION NO.    : 11/733710
DATED              : March 1, 2011
INVENTOR(S)        : Rimbaugh et al.

It is certified that error appears in the above-identified patent and that said Letters Patent is hereby corrected as shown below:

At Item 56, Page 2, Column 2, Line 71, under U.S. Patent Documents, change "Laufer et al." to -- Danek et al. --.

At Item 56, Page 3, Column 2, Line 49, under Other Publications, change "Cyanocrylate" to -- Cyanoacrylate --.

At Column 3, Line 25-26, change "administered" to -- administered. --.

At Column 8, Line 33, change "The apparatus of claim" to -- The method of claim --.

At Column 8, Line 36, change "The apparatus of claim" to -- The method of claim --.

At Column 8, Line 39, change "The apparatus of claim" to -- The method of claim --.

Signed and Sealed this
Fourth Day of October, 2011

David J. Kappos
*Director of the United States Patent and Trademark Office*